United States Patent
Boehmer et al.

(10) Patent No.: US 7,371,309 B2
(45) Date of Patent: May 13, 2008

(54) PURIFICATION OF DIFLUOROMETHANE BY EXTRACTIVE DISTILLATION

(75) Inventors: Sara W. Boehmer, Newark, DE (US); Barry Asher Mahler, Glen Mills, PA (US); Ralph Newton Miller, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/485,559

(22) PCT Filed: Aug. 12, 1998

(86) PCT No.: PCT/US98/16689

§ 371 (c)(1),
(2), (4) Date: Feb. 11, 2000

(87) PCT Pub. No.: WO99/07660

PCT Pub. Date: Feb. 18, 1999

(65) Prior Publication Data

US 2003/0116422 A1 Jun. 26, 2003

Related U.S. Application Data

(60) Provisional application No. 60/055,502, filed on Aug. 12, 1997.

(51) Int. Cl.
B01D 3/40 (2006.01)
C07C 17/386 (2006.01)
C07C 19/08 (2006.01)

(52) U.S. Cl. .......................... 203/57; 203/62; 203/63; 203/67; 203/68; 203/69; 203/70; 570/178

(58) Field of Classification Search .................. 203/68, 203/62–63, 67–70, 57; 570/178
See application file for complete search history.

(56) References Cited

U.S. PATENT DOCUMENTS

| | | | | | |
|---|---|---|---|---|---|
| 5,470,442 | A | * | 11/1995 | Mahler et al. | 203/56 |
| 5,534,151 | A | * | 7/1996 | Lee | 210/640 |
| 5,723,429 | A | * | 3/1998 | Mahler et al. | 510/408 |
| 5,785,822 | A | * | 7/1998 | Cerri et al. | 570/178 |
| 5,830,325 | A | * | 11/1998 | Mahler et al. | 203/71 |
| 6,156,161 | A | * | 12/2000 | Miller | 203/67 |
| 2003/0010618 | A1 | * | 1/2003 | Clemmer | 203/67 |

* cited by examiner

Primary Examiner—Virginia Manoharan

(57) ABSTRACT

The present invention provides extractive distillation processes for removing difluoromethane (HFC-32) from a mixture comprising HFC-32 and at least one of chlorodifluoromethane (CFC-12), 1,1,1-trifluoroethane (HFC-143a), chloropentafluoroethane (CFC-115), and pentafluoroethane (HFC-125) using hydrocarbon, chlorocarbon, and oxygen-containing extractive agents.

27 Claims, 1 Drawing Sheet

PURIFICATION OF DIFLUOROMETHANE BY EXTRACTIVE DISTILLATION

CROSS REFERENCE TO RELATED APPLICATIONS

This application claims the priority benefit of U.S. Provisional Application 60/055,502, filed Aug. 12, 1997.

FIELD OF THE INVENTION

The present invention relates to extractive distillation processes for purifying difluoromethane ($CF_2H_2$, HFC-32).

BACKGROUND OF THE INVENTION

New regulations have been established to protect the stratospheric ozone layer from possible damage by chlorofluorocarbons (CFCs). Highly purified HFC-32 is a hydrofluorocarbon (HFC) that is valuable as an etchant gas in plasma etching of materials used in the fabrication of semiconductor devices.

HFC-32 may be prepared by allowing methylene chloride ($CCl_2H_2$) to react with hydrogen fluoride (HF) in the presence of an oxidized metal catalyst of metals such as chromium, antimony, and tantalum. HFC-32 may also be co-produced with HFCs such as pentafluoroethane ($CF_3CF_2H$, HFC-125) by such metal mediated processes in which an HFC-125 precursor compound such as tetrachloroethylene ($CCl_2=CCl_2$) is utilized. The HFC-32 reaction product obtained from such processes may contain one or more of HFC-125, unreacted methylene chloride and HF, byproduct hydrogen chloride (HCl), and small amounts of organic byproducts such as 1,1,1-trifluoroethane ($CF_3CH_3$, HFC-143a), dichlorodifluoromethane ($CCl_2F_2$, CFC-12), chloropentafluoroethane ($CClF_2CF_3$, CFC-115), methyl chloride ($CH_3Cl$, HCC-40), methyl fluoride ($CH_3F$, HFC-41), trifluoromethane ($CF_3H$, HFC-23), chlorodifluoromethane ($CHClF_2$, HCFC-22), and 1,1-difluoroethane ($CF_2HCH_3$, HFC-152a). The presence of even trace amounts of such impurities in HFC-32 can be undesirable in the utilization of HFC-32 as an etchant gas in plasma processes employed in the semiconductor industry.

Casey et al., in PCT publication WO9703936 disclose processes for separation of HFC-32 and HFC-125 by azeotropic distillation of a low boiling HFC-32/HFC-125 azeotrope, separation of a mixture of HFC-32 and CFC-115 by azeotropic distillation of a low boiling HFC-32/CFC-115 azeotrope, separation of a mixture of HFC-32 and HFC-125 by extractive distillation employing methylene chloride as extractive agent, and separation of a mixture of HFC-32 and HFC-143a by employing CFC-115 as extractive agent.

Takahashi Reiji et al., in Japanese patent application JP 07291878, describe a process for the removal of HFC-143a, HFC-125, and methyl chloride from HFC-32 by extractive distillation. This process is characterized by employing at least one of 1,1-dichloro-1-fluoroethane ($CCl_2FCH_3$, HCFC-141b), dichloropentafluoropropane, trichlorotrifluoroethane, and 2,2-dichloro-1,1,1-trifluoroethane ($CHCl_2CF_3$, HCFC-123) as extractive agent. Using such CFC extractive agents is relatively expensive, and regulations concerning protection of the stratospheric ozone layer will cause CFCs to be phased out as commercial products thereby making CFCs unavailable or uneconomical for such a process.

The present invention solves problems associated with conventional purification methods and provides lower cost and more economical processes for separating HFC-32 from mixtures comprising HFC-32 and at least one halocarbon selected from HFC-143a, CFC-12, HFC-125, and CFC-115.

SUMMARY OF THE INVENTION

The present invention comprises a process for separating difluoromethane (HFC-32) from at least one halocarbon of a first mixture comprising difluoromethane (HFC-32) and halocarbon selected from the group consisting of dichlorodifluoromethane (CFC-12), 1,1,1-trifluoroethane (HFC-143a), chloropentafluoroethane (CFC-115), and pentafluoroethane (HFC-125), comprising the steps of:

contacting the first mixture with an extractive agent selected from the group consisting of:

hydrocarbon extractive agents comprising hydrocarbons having from 5 to 9 carbon atoms and having a normal boiling point greater than about 30° C. and less than about 155° C., oxygen-containing extractive agents comprising alcohols having a normal boiling point greater than about 60° C. and less than about 100° C. and represented by the formula $C_xH_{2x+1}OH$, wherein x is from 1 to 3, and ketones having a normal boiling point greater than about 50° C. and less than about 110° C. and represented by the formula $C_yH_{2y+1}COC_zH_{2z+1}$, wherein y and z are 1 or greater and y+z is at most 5, and chlorocarbon extractive agents comprising chlorocarbons having a normal boiling point greater than about 39° C. and less than about 150° C.

and represented by the formula $C_sH_{2s+2-t}Cl_t$, wherein s is 1 or 2 and t is from 2 to 4 to form a second mixture, separating difluoromethane (HFC-32) from at least one halocarbon of the second mixture by-extractively distilling the second mixture, and recovering difluoromethane (HFC-32) substantially free of at least one halocarbon, with the proviso that when the halocarbon is pentafluoroethane (HFC-125), the chlorocarbon extractive agent may not be methylene chloride.

BRIEF DESCRIPTION OF THE DRAWINGS

FIG. 1 is a schematic diagram of an extractive distillation system that can be used for practicing an aspect of the present process.

DETAILED DESCRIPTION

Figure 1:
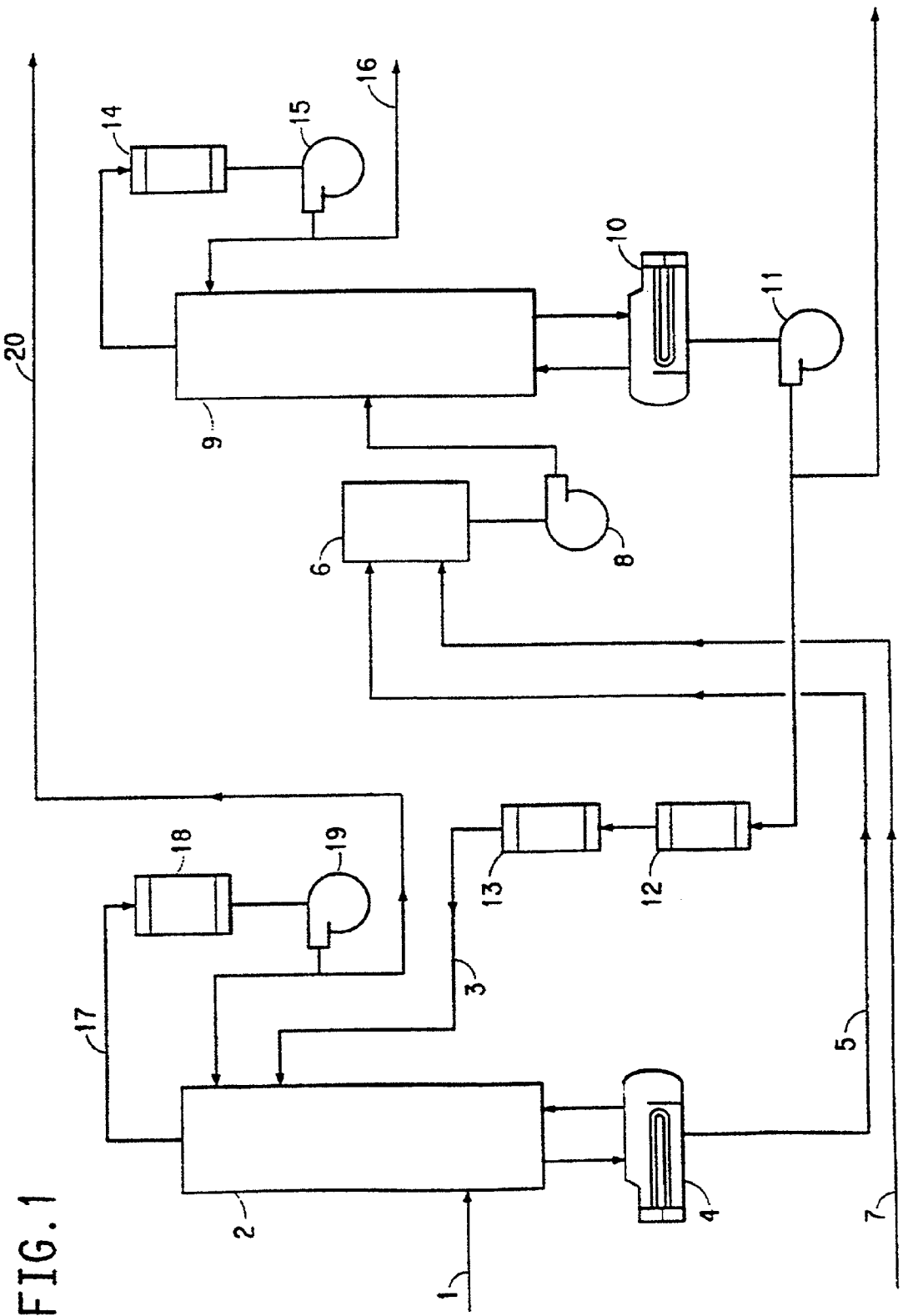
FIG. 1.

HFC-32 is commonly synthesized by fluorination of methylene chloride by a process wherein methylene chloride is allowed to react with hydrogen fluoride in the presence of a metal catalyst. HFC-32 so produced can contain a variety of impurities such as HCl, halocarbons such as HFC-143a and CFC-12, as well as unreacted methylene chloride and HF, among others. HFC-32 may also be co-produced with HFCs such as HFC-125 by such metal mediated processes in which an HFC-125 precursor compound such as tetrachloroethylene ($CCl_2=CCl_2$) is utilized. In the event of such HFC-32/HFC-125 co-production, HFC-32 product may additionally contain HFC-125 and HFC-125 byproducts such as CFC-115. While most of the process impurities can be removed by conventional distillation, the halocarbons CFC-12, HFC-143a, CFC-115, and HFC-125 are difficult if not impossible to remove by conventional distillation methods. This difficulty is due to the fact that CFC-12, HFC-143a, CFC-115, and HFC-125 form known azeotropes with HFC-32.

Halocarbon impurities of the present invention refers to at least one halocarbon selected from the group consisting of CFC-12, HFC-143a, CFC-115, and HFC-125. In their separate and pure states, HFC-32 and the halocarbon impurities have atmospheric boiling points of about −52° C. (HFC-32), −48° C. (HFC-125), −47° C. (HFC-143a), −39° C. (CFC-115), and −30° (CFC-12). However, a mixture comprising at least one such halocarbon and HFC-32 exhibits non-ideal vapor-liquid behavior such that the relative volatility of HFC-32 and halocarbon is very near 1.0. Conventional distillation procedures are incapable of efficiently separating HFC-32 from these halocarbons in instances where the relative volatility of HFC-32 and halocarbon is very near 1.0. The term conventional distillation refers to the practice where only the relative volatility of the components of a mixture to be separated is used to separate the components.

To determine the relative volatility of HFC-32 and halocarbon, a method known as the PTx method was used. Use of the PTx method is described in detail in "Phase Equilibrium in Process Design," Wiley-Interscience Publisher, 1970, written by Harold R. Null, pages 124 through 126, hereby incorporated by reference. In the PTx method, the total absolute pressure in a cell of known volume is measured at a constant temperature for various known binary compositions of HFC-32 and halocarbon. These total pressure measurements are converted into equilibrium vapor and liquid compositions by employing an activity coefficient equation model such as the Non-Random, Two Liquid (NRTL) equation, which represents liquid phase non-idealities. Use of an activity coefficient equation such as the NRTL equation, is described in "The Properties of Gases and Liquids," 4$^{th}$ edition, published by McGraw Hill, written by Reid, Prausnitz and Poling, pages 241 through 387; and in "Phase Equilibria in Chemical Engineering," published in 1985 by Butterworth Publishers, written by Stanley M. Walas, pages 165 through 244. Both aforementioned references are hereby incorporated by reference. Without wishing to be bound by theory, it is believed that the NRTL equation can sufficiently predict the relative volatilities of mixtures comprising HFC-32 and the halocarbon impurities of the present invention.

The results of PTx measurements and the above calculations indicate that the relative volatilities of HFC-32 and halocarbon are equal to 1 for given compositions of HFC-32 and halocarbon over a range of temperatures. Relative volatilities of 1 in a mixture indicate the formation of an azeotrope. The results of PTx measurements and the above calculations indicate that the composition of the azeotropes varies with temperature. Tables 1 through 4 show the results of these calculations, specifically, how the composition of the HFC-32/halocarbon azeotropes varies with temperature. Because of the formation of azeotropes, it is difficult, if not impossible, to completely separate HFC-32 from halocarbon by conventional distillation techniques at temperatures and pressures within the ranges shown in Tables 1 through 4.

By azeotrope or azeotropic composition is meant a substantially constant boiling liquid mixture of two or more substances that behaves as a single substance. One way to characterize an azeotropic composition or mixture is that the vapor produced by partial evaporation or distillation of the liquid has substantially the same composition as the liquid from which it was evaporated or

TABLE 1

Variation of the HFC-32/CFC-12 Azeotropic Composition with Temperature

| Temp. (° C.) | CFC-12 Mole Fraction, Liquid Phase | CFC-12 Mole Fraction, Vapor Phase | HFC-32 Mole Fraction, Liquid Phase | HFC-32 Mole Fraction, Vapor Phase | Vapor Pressure (psia) | Relative Volatility HFC-32/ CFC-12 |
|---|---|---|---|---|---|---|
| −80.0 | 0.1771 | 0.1771 | 0.8229 | 0.8229 | 3.0 | 1.000 |
| −60.0 | 0.1802 | 0.1802 | 0.8198 | 0.8198 | 10.3 | 1.000 |
| −40.0 | 0.1757 | 0.1757 | 0.8243 | 0.8243 | 27.6 | 1.000 |
| −20.0 | 0.1647 | 0.1647 | 0.8353 | 0.8353 | 62.1 | 1.000 |
| 0.0 | 0.1480 | 0.1480 | 0.8520 | 0.8520 | 122.5 | 1.000 |
| 10.0 | 0.1376 | 0.1376 | 0.8624 | 0.8624 | 165.6 | 1.000 |
| 20.0 | 0.1255 | 0.1255 | 0.8745 | 0.8745 | 219.1 | 1.000 |
| 40.0 | 0.0946 | 0.0946 | 0.9054 | 0.9054 | 363.9 | 1.000 |
| 50.0 | 0.0736 | 0.0736 | 0.9265 | 0.9265 | 458.9 | 1.000 |
| 55.0 | 0.0602 | 0.0602 | 0.9398 | 0.9398 | 513.0 | 1.000 |

Pressure/composition measurements were taken at 0° C. and 40° C. and extrapolated over the temperature range using the aforementioned calculations.

TABLE 2

Variation of the HFC-32/HFC-143a Azeotropic Composition with Temperature

| Temp. (° C.) | HFC-143a Mole Fraction, Liquid Phase | HFC-143a Mole Fraction, Vapor Phase | HFC-32 Mole Fraction, Liquid Phase | HFC-32 Mole Fraction, Vapor Phase | Vapor Pressure (psia) | Relative Volatility HFC-32/ HFC-143a |
|---|---|---|---|---|---|---|
| −80.0 | 0.2830 | 0.2830 | 0.7170 | 0.7170 | 2.9 | 1.000 |
| −60.0 | 0.2334 | 0.2334 | 0.7666 | 0.7666 | 9.7 | 1.000 |
| −50.0 | 0.2078 | 0.2078 | 0.7922 | 0.7922 | 16.4 | 1.000 |
| −40.0 | 0.1818 | 0.1818 | 0.8182 | 0.8182 | 26.2 | 1.000 |
| −20.0 | 0.1286 | 0.1286 | 0.8714 | 0.8714 | 59.3 | 1.000 |
| 0.0 | 0.0736 | 0.0736 | 0.9265 | 0.9265 | 118.2 | 1.000 |

TABLE 2-continued

Variation of the HFC-32/HFC-143a Azeotropic Composition with Temperature

| Temp. (° C.) | HFC-143a Mole Fraction, Liquid Phase | HFC-143a Mole Fraction, Vapor Phase | HFC-32 Mole Fraction, Liquid Phase | HFC-32 Mole Fraction, Vapor Phase | Vapor Pressure (psia) | Relative Volatility HFC-32/ HFC-143a |
|---|---|---|---|---|---|---|
| 10.0 | 0.0448 | 0.0448 | 0.9553 | 0.9553 | 160.7 | 1.000 |
| 20.0 | 0.0144 | 0.0144 | 0.9856 | 0.9856 | 213.9 | 1.000 |
| 23.0 | 0.0048 | 0.0048 | 0.9952 | 0.9952 | 232.2 | 1.000 |

Pressure/composition measurements were taken at −17° C. and 40° C. and extrapolated over the temperature range using the aforementioned calculations.

TABLE 3

Variation of the HFC-32/CFC-115 Azeotropic Composition with Temperature

| Temp. (° C.) | CFC-115 Mole Fraction, Liquid Phase | CFC-115 Mole Fraction, Vapor Phase | HFC-32 Mole Fraction, Liquid Phase | HFC-32 Mole Fraction, Vapor Phase | Vapor Pressure (psia) | Relative Volatility HFC-32/ CFC-115 |
|---|---|---|---|---|---|---|
| −80.0 | 0.3040 | 0.3040 | 0.6960 | 0.6960 | 3.4 | 1.000 |
| −60.0 | 0.3075 | 0.3075 | 0.6925 | 0.6925 | 11.7 | 1.000 |
| −40.0 | 0.3023 | 0.3023 | 0.6977 | 0.6977 | 31.5 | 1.000 |
| −20.0 | 0.2922 | 0.2922 | 0.7078 | 0.7078 | 70.6 | 1.000 |
| 0.0 | 0.2786 | 0.2786 | 0.7215 | 0.7215 | 138.3 | 1.000 |
| 10.0 | 0.2703 | 0.2703 | 0.7297 | 0.7297 | 185.9 | 1.000 |
| 20.0 | 0.2607 | 0.2607 | 0.7393 | 0.7393 | 244.3 | 1.000 |
| 40.0 | 0.2345 | 0.2345 | 0.7655 | 0.7655 | 398.4 | 1.000 |
| 60.0 | 0.1848 | 0.1848 | 0.8152 | 0.8152 | 606.3 | 1.000 |
| 80.0 | 0.0071 | 0.0071 | 0.9929 | 0.9929 | 866.1 | 1.000 |

Pressure/composition measurements were taken at 0° C. and 39° C. and extrapolated over the temperature range using the aforementioned calculations.

TABLE 4

Variation of the HFC-32/HFC-125 Azeotropic Composition with Temperature

| Temp. (° C.) | HFC-125 Mole Fraction, Liquid Phase | HFC-125 Mole Fraction, Vapor Phase | HFC-32 Mole Fraction, Liquid Phase | HFC-32 Mole Fraction, Vapor Phase | Vapor Pressure (psia) | Relative Volatility HFC-32/ HFC-125 |
|---|---|---|---|---|---|---|
| −80.0 | 0.1514 | 0.1514 | 0.8486 | 0.8486 | 2.8 | 1.000 |
| −60.0 | 0.1359 | 0.1359 | 0.8641 | 0.8641 | 9.5 | 1.000 |
| −40.0 | 0.1165 | 0.1165 | 0.8835 | 0.8835 | 25.9 | 1.000 |
| −20.0 | 0.0952 | 0.0952 | 0.9048 | 0.9048 | 59.1 | 1.000 |
| 0.0 | 0.0746 | 0.0746 | 0.9254 | 0.9254 | 118.2 | 1.000 |
| 20.0 | 0.0592 | 0.0592 | 0.9408 | 0.9408 | 214.2 | 1.000 |
| 40.0 | 0.0590 | 0.0590 | 0.9410 | 0.9410 | 360.0 | 1.000 |
| 50.0 | 0.0737 | 0.0737 | 0.9263 | 0.9263 | 456.7 | 1.000 |

Pressure/composition measurements were taken at −38, −15, 15, and 44° C. and extrapolated over the temperature range using the aforementioned calculations.

distilled, i.e., the mixture distills/refluxes without compositional change. Constant boiling compositions are characterized as azeotropic because they exhibit either a maximum or minimum boiling point relative to that of the pure components. Azeotropic compositions are also characterized by a minimum or a maximum in the vapor pressure measurements relative to the vapor pressure of the pure components in a PTx cell as a function of composition at a constant temperature.

The fact that the HFC-32/halocarbon low-boiling (high pressure) azeotropic compositions vary depending on temperature and pressure provides a method of separating and partially purifying the HFC-32 from halocarbon. This method is known as azeotropic distillation and allows for partial separation of the azeotrope into its components within a distillation column. If the HFC-32/halocarbon azeotropic composition formed under one temperature/pressure is then distilled under a different temperature/pressure, the composition of the azeotrope will change such that one component, HFC-32 or halocarbon, is now in excess relative to the newly-formed azeotropic composition. By excess component is meant the component of an azeotropic composition which is in excess of the quantity of that component which is required for azeotropic formation at a given temperature and pressure. The newly formed azeotropic composition may then be distilled overhead while the excess component is recovered as column bottoms. For example, a distillation column can be operated at a temperature and pressure that causes the azeotropic composition to form. If the quantity of HFC-32 is relatively large in comparison to, for instance, HFC-143a, i.e. the concentration of HFC-32 is greater than that in the azeotropic composition, the HFC-32 can be removed in substantially pure form from the bottom of the column, while the azeotropic composition is removed from the top of the column.

The results of PTx measurements and the aforementioned calculations for HFC-32 and halocarbon in the presence of various extractive distillation agents are summarized in Tables 5 through 8. Shown are activity coefficients at 0° C. for HFC-32/CFC-12 (Table 5), HFC-32/HFC-143a (Table 6), HFC-32/CFC-115 (Table 7) and HFC-32/HFC-125 (Table 8) at infinite dilution in the listed extraction agent. Also shown are the ratios of HFC-32 activity coefficient to halocarbon activity coefficient (relative volatility). The ratio of the activity coefficient for HFC-32 at infinite dilution in an extractive agent relative to the activity coefficient of halocarbon at infinite dilution in the proposed extractive agent is the relative volatility of HFC-32 and halocarbon in the presence of the extractive agent.

TABLE 5

Extractive Agents for HFC-32/CFC-12

| Extractive Agent | Formula | NBP* (° C.) | HFC-32 | CFC-12 | Ratio |
|---|---|---|---|---|---|
| n-Pentane | $C_5H_{12}$ | 36.1 | 7.04 | 1.38 | 5.10 |
| Methylcyclopentane | $C_6H_{12}$ | 71.8 | 9.30 | 1.86 | 5.00 |
| n-Hexane | $C_6H_{14}$ | 68.7 | 7.25 | 1.48 | 4.90 |
| Methanol | $CH_3OH$ | 64.6 | 3.89 | 10.82 | 0.36 |
| Acetone | $CH_3COCH_3$ | 56.3 | 0.77 | 3.23 | 0.24 |
| Methylene Chloride | $CH_2Cl_2$ | 39.8 | 2.77 | 4.04 | 0.69 |

*NBP = Normal Boiling Point (temperature at which vapor pressure is equal to 1 atmosphere)

TABLE 6

Extractive Agents for HFC-32/HFC-143a

| Extractive Agent | Formula | NBP (° C.) | HFC-32 | HFC-143a | Ratio |
|---|---|---|---|---|---|
| n-Pentane | $C_5H_{12}$ | 36.1 | 7.04 | 4.79 | 1.47 |
| Cyclopentane | $C_5H_{10}$ | 49.3 | 10.78 | 7.91 | 1.36 |
| Methylcyclopentane | $C_6H_{12}$ | 71.8 | 9.30 | 6.82 | 1.36 |
| n-Hexane | $C_6H_{14}$ | 68.7 | 7.25 | 5.22 | 1.39 |
| Methanol | $CH_3OH$ | 64.6 | 3.89 | 7.71 | 0.50 |
| Acetone | $CH_3COCH_3$ | 56.3 | 0.77 | 1.78 | 0.43 |
| Methylene Chloride | $CH_2Cl_2$ | 39.8 | 2.77 | 4.82 | 0.57 |

TABLE 7

Extractive Agents for HFC-32/CFC-115

| Extractive Agent | Formula | NBP (° C.) | HFC-32 | CFC-115 | Ratio |
|---|---|---|---|---|---|
| n-Pentane | $C_5H_{12}$ | 36.1 | 7.04 | 6.61 | 1.07 |
| Cyclopentane | $C_5H_{10}$ | 49.3 | 10.78 | 5.95 | 1.81 |
| n-Hexane | $C_6H_{14}$ | 68.7 | 7.25 | 3.94 | 1.84 |
| Methanol | $CH_3OH$ | 64.6 | 3.89 | 37.45 | 0.10 |

TABLE 7-continued

Extractive Agents for HFC-32/CFC-115

| Extractive Agent | Formula | NBP (° C.) | HFC-32 | CFC-115 | Ratio |
|---|---|---|---|---|---|
| Acetone | $CH_3COCH_3$ | 56.3 | 0.77 | 12.03 | 0.064 |
| Methylene Chloride | $CH_2Cl_2$ | 39.8 | 2.77 | 19.55 | 0.14 |

TABLE 8

Extractive Agents for HFC-32/HFC-125

| Extractive Agent | Formula | NBP (° C.) | HFC-32 | HFC-125 | Ratio |
|---|---|---|---|---|---|
| n-Pentane | $C_5H_{12}$ | 36.1 | 7.04 | 9.34 | 0.75 |
| Cyclopentane | $C_5H_{10}$ | 49.3 | 10.78 | 11.04 | 0.98 |
| n-Hexane | $C_6H_{14}$ | 68.7 | 7.25 | 6.65 | 1.09 |
| Methanol | $CH_3OH$ | 64.6 | 3.89 | 3.94 | 0.99 |
| Acetone | $CH_3COCH_3$ | 56.3 | 0.77 | 0.87 | 0.89 |
| Methylene Chloride | $CH_2Cl_2$ | 39.8 | 2.77 | 9.53 | 0.29 |

The problems encountered upon conventional distillation of HFC-32/halocarbon, such as the need for taller columns, higher energy input, and lower resultant HFC-32 recovery, can be solved by practicing the present inventive extractive distillation process. By extractive distillation is meant a process in which an extractive agent is introduced at an upper feed point of a distillation column, whereas the mixture requiring separation is introduced at the same point or preferably, at a relatively lower feed point of the column. The substantially liquid extractive agent passes downwardly through trays or packing in the column and exits the column bottoms with one or more components of the mixture to be separated. While in the presence of the extractive agent, at least one of the components of an initial mixture to be separated becomes relatively more volatile compared to the other components of the mixture, with that more volatile component of the initial mixture exiting the column overheads. Extractive distillation may be employed when the components of a mixture have relative volatilities that do not afford effective separation of the components by conventional distillation. In extractive distillation, an extractive agent is used which causes the relative volatilities of the components in a mixture to be altered such that the resultant relative volatilities, i.e., that of components of the mixture in the presence of the extractive agent, become sufficient to permit separation of the components by distillation techniques. The difficulty in applying this method is that there is no way of predicting which, if any, compound will be an effective extractive distillation agent for a given azeotropic composition.

The present inventors have discovered through experimentation that the relative volatility of compositions comprising HFC-32 and at least one of the halocarbons CFC-12, HFC-143a, CFC-115, and HFC-125 can be altered from 1.0 in the presence of extractive agents selected from: hydrocarbons having 5 to 9 carbon atoms and having a normal boiling point greater than about 30° C. and less than about 155° C.; alcohols having a normal boiling point greater than about 60° C. and less than about 100° C. and represented by the formula $C_xH_{2x+1}OH$, wherein x is from 1 to 3; ketones having a normal boiling point greater than about 50° C. and less than about 110° C. and represented by the formula $C_yH_{2y+1}COC_zH_{2z+1}$, wherein y and z are 1 or greater and y+z is at most 5; and chlorocarbons having a normal boiling point greater than about 39° C. and less than about 150° C. and represented by the formula $C_sH_{2s+2-t}Cl_t$, wherein s is 1 or 2 and t is from 2 to 4.

This discovery allows for separation of HFC-32 from a first mixture comprising HFC-32 and halocarbon by extractive distillation in the presence of an appropriate extractive agent. The appropriate extractive agent for a first mixture comprising HFC-32 and halocarbon is one which causes the relative volatility of the HFC-32 and halocarbon to be greater than 1.0, with the HFC-32 being more volatile, thus permitting HFC-32 to be removed from the top of the distillation zone. Alternately, the appropriate extractive agent for a first mixture comprising HFC-32 and halocarbon is one which causes the relative volatility of the HFC-32 and halocarbon to be less than 1.0, with the HFC-32 being less volatile, thus permitting halocarbon to be removed from the top of the distillation zone and HFC-32 to be removed from the bottom of the distillation zone together with the extractive agent. In order for an extractive agent to be effective in separating HFC-32 from halocarbon by extractive distillation, the relative volatility of the HFC-32 and halocarbon in the presence of the extractive agent must theoretically be greater than or less than about 1.0. For practical purposes it must generally be greater than about 1.1 or less than about 0.9. Normally, for commercially useful separation of 32 and halocarbon to occur in the present extractive distillation process, this relative volatility will be greater than about 1.3 or less than about 0.5, and still more preferably it will be greater than about 2.0 or less than about 0.3. When more than one halocarbon is present in a first mixture comprising HFC-32 and halocarbon, an effective extractive agent is one for which the relative volatility for each HFC-32/halocarbon pair of the first mixture satisfies the aforementioned relative volatility criteria in the same direction relative to 1.0. For instance, when CFC-12 and HFC-143a halocarbon impurities are both present in HFC-32 concurrently, an effective extractive agent is one for which the relative volatilities for both HFC-32/CFC-12 and HFC-32/HFC-143a are greater than 1.0.

The present inventors have discovered that at least one halocarbon selected from the group consisting of CFC-12, HFC-143a, CFC-115, and HFC-125 can be efficiently separated from HFC-32 by using an extractive distillation process with a hydrocarbon extractive agent comprising at least one linear, branched, or cyclic aliphatic hydrocarbon having a normal boiling point greater than about 30° C. and less than about 155° C. selected from the families of hydrocarbons known as pentanes, hexanes, heptanes, octanes, and nonanes. Hydrocarbon extractive agents with a normal boiling point between about 60° C. and 110° C. are especially useful. Preferred hydrocarbon extractive agents are n-pentane, cyclopentane, methylcyclopentane, n-hexane, cyclohexane and n-heptane. Hydrocarbon extractive agents used in the present invention are generally commercially available. Commercial grade hydrocarbons, such as Optima® grade Hexane available from Fisher Scientific, Pittsburgh, Pa., USA, containing 2-methylpentane (0.2 volume %), 3-methylpentane (3.5%), n-hexane (85.4%), methylcyclopentane (10.9%), may be employed as hydrocarbon extractive agent in the process of the present invention. The extractive agent is chosen such that under the conditions of the extractive distillation, the extractive agent is not in the solid phase, i.e., the extractive agent does not freeze and form solid in the apparatus.

The present inventors have discovered that at least one halocarbon selected from the group consisting of CFC-12, HFC-143a, CFC-115, and HFC-125 can be efficiently separated from HFC-32 by using an extractive distillation process with an oxygen-containing extractive agent comprising: alcohols having a normal boiling point greater than about 60° C. and less than about 100° C. and represented by the formula $C_xH_{2x+1}OH$, wherein x is from 1 to 3; and ketones having a normal boiling point greater than about 50° C. and less than about 110° C. and represented by the formula $C_yH_{2y+1}COC_zH_{2z+1}$, wherein y and z are 1 or greater and y+z is at most 5. Representative oxygen-containing extractive agents are methanol, ethanol, n-propanol, iso-propanol, propanone (acetone), and butanone.

The present inventors have discovered that at least one halocarbon selected from the group consisting of CFC-12, HFC-143a, CFC-115, and HFC-125 can be efficiently separated from HFC-32 by using an extractive distillation process with a chlorocarbon extractive agent comprising chlorocarbons having a normal boiling point greater than about 39° C. and less than about 150° C. and represented by the formula $C_sH_{2s+2-t}Cl_t$, wherein s is 1 or 2 and t is from 2 to 4. Representative chlorocarbon extractive agents are methylene chloride ($CH_2Cl_2$), chloroform (trichloromethane, $CHCl_3$), carbon tetrachloride ($CCl_4$), dichloroethane ($CH_3CHCl_2$, $CH_2ClCH_2Cl$), trichloroethane ($CH_3CCl_3$, $CHCl_2CH_2Cl$), and tetrachloroethane ($CH_2ClCCl_3$, $CHCl_2CHCl_2$).

The extractive distillation processes of the present invention for separating HFC-32 from at least one halocarbon comprise the steps of:

a) contacting a HFC-32/halocarbon first mixture with an extractive agent to form a second mixture, and b) separating the HFC-32 from at least one halocarbon of the second mixture by extractively distilling the second mixture in an extractive distillation zone thereby recovering HFC-32 substantially free of at least one halocarbon:

as an overhead product, and from the bottom of the zone a third mixture comprising the extractive agent and halocarbon for the embodiment of the present invention wherein the HFC-32 and halocarbon relative volatility is greater than 1.0, or as a bottoms product together with extractive agent, and as a third mixture an overhead product comprising halocarbon for the embodiment of the present invention wherein the HFC-32 and halocarbon relative volatility is less than 1.0.

In each of the aforementioned embodiments, the extractive agent is preferably recycled. For instance, for extractive agents causing a HFC-32 and halocarbon relative volatility greater than 1.0, extractive agent will be recovered from the extractive distillation step together with halocarbon, and may be further purified (e.g., by conventional distillation) and recycled to the contacting step. For extractive agents causing HFC-32 and halocarbon relative volatility less than 1.0, extractive agent will be recovered from the extractive distillation step together with HFC-32, and may be further purified (e.g., by conventional distillation) and recycled to the contacting step leaving HFC-32 substantially free of halocarbon.

By substantially free or substantially pure, it is meant that the HFC-32 product contains less than about 0.1 weight % halocarbon, and preferably less than about 50 parts per million by weight (ppmw) of halocarbon. Higher purity HFC-32 for use as plasma etchant gas, e.g., containing 0.1 ppmw or less of halocarbon, may be produced by the present extractive distillation process by varying the extractant flow and distillation column dimensions.

While the present process may be used to purify a wide range of HFC-32 compositions containing one or more of the present halocarbons, it is preferred that the HFC-32 content be greater than about 90 mole % and that the halocarbon content be less than about 10 mole %. If desired, the aforementioned azeotropic distillation method can be used for reducing the initial quantity of halocarbon and other impurities in the HFC-32 composition. That is, conventional distillation can be used for removing relatively large or bulk quantities of impurities from the first mixture which in turn is processed in accordance with the inventive process for separating HFC-32 from halocarbon.

Extractive distillation is typically performed by operating a continuous distillation column, which comprises a multi-stage distillation column with two feed points. Extractive agent is introduced at a first feed point on the column which is located at the same height, more preferably above, a second feed point that is used for introducing the HFC-32/halocarbon mixture to be separated. The distillation column further comprises a reboiler and an overhead condenser for returning reflux to the column.

In one embodiment of the present process, hydrocarbon extractive agent is introduced at an upper feed point of an extractive distillation column, whereas the first mixture requiring separation, e.g., comprising HFC-32 and halocarbon, is introduced at a relatively lower point in the column. The hydrocarbon extractive agent passes downwardly through trays in the column and contacts the first mixture thereby forming a second mixture. While in the presence of the hydrocarbon extractive agent, HFC-32 is relatively more volatile than halocarbon, thereby causing substantially pure HFC-32 to exit the top of the column. HFC-32 exiting the top of the column can be condensed by reflux condensers. At least a portion of this condensed stream can be returned to the top of the column as reflux, and the remainder recovered as substantially pure HFC-32 product. Hydrocarbon extractive agent, halocarbon, and comprise a third mixture that exits from the bottom of the column, which can then be passed to a stripper or distillation column for separation by using conventional distillation or other known methods. The hydrocarbon extractive agent can be recycled to the extractive distillation column.

In another embodiment of the present process, oxygen-containing or chlorocarbon extractive agent is introduced at an upper feed point of an extractive distillation column, whereas the first mixture requiring separation, e.g., comprising HFC-32 and halocarbon, is introduced at a relatively lower point in the column. The oxygen-containing or chlorocarbon extractive agent passes downwardly through trays in the column and contacts the first mixture thereby forming a second mixture. While in the presence of oxygen-containing or chlorocarbon extractive agent, halocarbons are relatively more volatile than HFC-32, thereby causing halocarbons to exit the top of the column. Oxygen-containing or chlorocarbon extractive agent and substantially pure HFC-32 comprise a third mixture that exits from the bottom of the column, which can in turn be passed to a stripper or distillation column for separation by using conventional distillation or other known methods. The oxygen-containing or chlorocarbon extractive agent can be recycled to the extractive distillation column.

The ratio of the material exiting the top of the extractive distillation column, which is then condensed and in turn returned to the column, to the amount of material that is removed as product is commonly referred to as the reflux ratio. The reflux ratio will define the physical characteristics of the extractive distillation column. In general, an increase in the reflux ratio will in turn cause an increase in the purity of the overhead stream (HFC-32 or halocarbon) by reducing or eliminating the quantity of extractive agent and other impurities in the overhead stream.

The specific conditions that can be used for practicing the invention depend upon a number of interrelated design parameters such as the diameter of the column, feed point location on the column, and the number of separation stages in the column, among other parameters. The operating pressure of the distillation system may range from about 15 to about 350 psia, normally about 50 to 300 psia. The temperature and heat transfer area of the overhead condenser is normally sufficient to substantially fully condense the overhead product, or is optionally sufficient to achieve the desired reflux ratio by partial condensation.

The effective amount of extractive agent can vary widely. In general, increasing the amount of extractive agent will increase the purity of the overhead HFC-32 or halocarbon stream. Typically, the ratio of extractive agent to HFC-32 ranges from about $1/1$ to $10/1$ on a weight basis; however, higher ratios can be employed.

The temperature that is employed at a given step in the inventive process may vary, as column operating temperature is a function of the pressure and design characteristics of the distillation column, e.g., the ratio of extractive agent to the first mixture.

The present inventive process can be better understood by reference to FIG. 1. FIG. 1 schematically illustrates a system which can be used for performing the embodiment of the present extractive distillation process wherein HFC-32 is separated from a first mixture comprising HFC-32 and halocarbon using a hydrocarbon extractive agent.

A first mixture comprising HFC-32 and halocarbon impurity is supplied via conduit 1 to extraction column 2. At least one liquid hydrocarbon extractive agent is supplied via conduit 3 to the extraction column 2, and introduced into column 2 at a location above the mixture 1. A second mixture comprising the hydrocarbon extractive agent and halocarbon is removed from the bottom of column 2 and transported to steam heated reboiler 4. In some cases, reboiler 4 is attached to extractive column 2. The second mixture is supplied via conduit 5 to a feed tank 6. Supplemental liquid hydrocarbon extractive agent is also supplied to feed tank 6 via conduit 7 thereby forming a hydrocarbon extractive agent recycle. A pump 8 transports the hydrocarbon extractive agent recycle to a stripping mixture column 9. Stripping column 9 separates the hydrocarbon extractive agent from other materials. Hydrocarbon extractive agent is removed from column 9 and supplied to a second steam heated reboiler 10. In some cases, the reboiler 10 is attached to column 9. Pump 11 transports the hydrocarbon extractive agent from the reboiler 10 through a cold water chiller 12, and then to chiller 13. If necessary, excess quantities of hydrocarbon extractive agent can be purged prior to reaching chiller 12. Typically, chiller 13 is operated at a temperature of about –25° C. After exiting chiller 13, the hydrocarbon extractive agent is supplied via conduit 3 into extraction column 2.

Halocarbon exits from the top of stripping column 9 as an off gas, and is introduced into condenser 14, which is typically operated at a temperature of about –25° C. While under reflux conditions, pump 15 returns a portion of the halocarbon to the stripping column 9. The remaining portion of the halocarbon can be removed from the system via conduit 16.

An off gas of HFC-32 that is substantially free of halocarbon and other compounds is removed from extraction column 2. The HFC-32 is transported via conduit 17 to condenser 18. Condenser 18 is typically operated at a temperature of about −25° C. While under reflux conditions, pump 19 returns a portion of the HFC-32 to extraction column 2. The HFC-32 can be removed from the system via conduit 20.

EXAMPLES

The following Examples are provided to illustrate certain aspects of the present invention, and do not limit the scope of the invention. In the following Examples, each column stage is based upon a 100% operational or performance efficiency. Differing column designs and operating conditions are employed using different extractive agents in order to maximize the performance of each distillation. In all examples, the total theoretical stages includes condenser and reboiler, with the condenser counted as stage No. 1.

Example 1

In this Example of the invention, a low boiler distillation column and an extractive distillation column were used to purify a feed stream composed of 10 lb/hr of crude HFC-32. The crude feed contained 0.00022 lb/hr of CFC-12, a CFC-12 concentration of 22 parts per million by weight (ppmw), and 0.00229 lb/hr of HFC-143a, a HFC-143a concentration of 229 ppmw. Other feed impurities were: 678 ppmw HFC-23 ($CHF_3$), 63 ppmw HFC-41 ($CH_3F$), 46 ppmw HCFC-22 ($CHClF_2$), 13 ppmw HCC-40 ($CH_3Cl$), 6 ppmw HFC-134a ($CH_2HCF_3$), 4 ppmw HFC-134 ($CHF_2CHF_2$), and 0.2 ppmw HFC-152a ($CHF_2CH3$). The low boiler column was a packed column containing 23 theoretical stages. The crude feed stream was introduced at stage 12 of the low boiler column. The low boiler column condenser pressure was maintained at 190 psia. The distillate temperature was 15° C. and the bottom column temperature was 16° C. The low boiler column boilup rate was set so as to give at least 40 lb/hr of internal reflux in the column (calculated based on condenser duty). The distillate takeoff rate was controlled at 0.5 lb/hr. Under these conditions, the low boiling impurities in the crude feed stream left the top of the low boiler column while the HFC-32 and its near boiling and high boiling impurities left with the bottoms stream. A sample of the bottoms stream indicated the following composition: 99.9785 wt % HFC-32, 172 ppmw HFC-143a, 25 ppmw HCC-40, 12 ppmw HCFC-22, 5 ppmw HFC-134a, and 1 ppmw HFC-134.

The extractive distillation column was a packed column containing 54 theoretical stages. The bottoms stream from the low boiler column was introduced at stage 33 of the extractive distillation column and n-hexane extractive agent was introduced at stage 13 at 150 lb/hr. The column condenser pressure was maintained at 84.7 psia. The distillate temperature was −9° C., and the bottom column temperature was 110° C. Under these operating conditions, the HFC-32 product left in the overhead stream from the column and the n-hexane containing HFC-143a exited in the bottom stream. The extractive agent flow rate was set so as to meet a composition of less than 25 ppmw of HFC-143a in the overhead HFC-32 product. The column boilup rate of 28 lb/hr of steam to the reboiler was set so as to give sufficient reflux to meet a composition of less than 5 ppmw extractive agent in the HFC-32 overhead product. The distillate rate was controlled to recover 9 lb/hr of HFC-32 in the distillate overhead stream. The column diameter was chosen so as to have an F-factor of 0.59 or below. HFC-32 of 99.998 wt % purity was recovered with 99.89% recovery of the HFC-32 fed to the extractive distillation column. The HFC-32 product contained 16 ppmw of HFC-143a, 1 ppmw of HCC-40, and 2 ppmw of n-hexane.

Example 2

In this Example of the invention, a low boiler distillation column and an extractive distillation column were used to purify a feed stream composed of 20 lb/hr of crude HFC-32. The crude feed contained 0.00148 lb/hr of CFC-12, a CFC-12 concentration of 74 parts per million by weight (ppmw), and 0.00270 lb/hr of HFC-143a, a HFC-143a concentration of 135 ppmw. Other feed impurities were: 31 ppmw n-hexane ($C_6H_{14}$), 21 ppmw HCFC-22 ($CHClF_2$), 7 ppmw HCC-40 ($CH_3Cl$), 1 ppmw HFC-134a ($CH_2FCF_3$), and 1 ppmw CFC-13 ($CClF_3$). The low boiler column was a packed column containing 23 theoretical stages. The crude feed stream was introduced at stage 12 of the low boiler column. The low boiler column condenser pressure was maintained at 190 psia. The distillate temperature was 15° C. and the bottom column temperature was 16° C. The low boiler column boilup rate was set so as to give at least 40 lb/hr of internal reflux in the column (calculated based on condenser duty). The distillate takeoff rate was controlled at 0.2 lb/hr. Under these conditions, the low boiling impurities in the crude feed stream left the top of the low boiler column while the HFC-32 and its near boiling and high boiling impurities left with the bottoms stream. A sample of the bottoms stream indicated the following composition: 99.9823 wt % HFC-32, 121 ppmw HFC-143a, 24 ppmw n-hexane, 20 ppmw HCFC-22, 7 ppmw HCC-40, and 5 ppmw CFC-12.

The extractive distillation column was a packed column containing 54 theoretical stages. The bottoms from the low boiler column was introduced at stage 33 of the extractive distillation column and the n-hexane extractive agent was introduced at stage 13 at 150 lb/hr. The column condenser pressure was maintained at 84.7 psia. The distillate temperature was −9° C., and the bottom column temperature was 120° C. Under these operating conditions, the HFC-32 product left in the overhead stream from the column and the n-hexane containing CFC-12 and HFC-143a exited in the bottom stream. The extractive agent flow rate was set so as to meet a composition of less than 40 ppmw of HFC-143a in the overhead HFC-32 product. The column boilup rate of 28 lb/hr of steam to the reboiler was set so as to give sufficient reflux to meet a composition of less than 5 ppmw extractive agent in the HFC-32 overhead product. The distillate rate was controlled to recover 19.5 lb/hr of HFC-32 in the distillate overhead stream. The column diameter was chosen so as to have an F-factor of 0.59 or below. HFC-32 of 99.9964 wt % purity was recovered with 98.75% recovery of HFC-32 fed to the extractive distillation column. The HFC-32 product contained 30 ppmw of HFC-143a and 6 ppmw of other unknown impurities; CFC-12 was below detectable limits in the product.

Examples 3-16 Comparative Examples 1-4

The following examples are calculated, theoretical examples employing the aforementioned NRTL interaction parameters. The examples are based on 1000 lb/hr of crude HFC-32 feed containing selected halocarbon impurities. No other impurities were considered to be present in the feed. Also included are calculated, theoretical Comparative Examples employing the aforementioned NRTL interaction parameters.

TABLE 9

Comparative Examples - Distillation Using No Extractive Agent

|  | Comparative Example 1 | Comparative Example 2 | Comparative Example 3 | Comparative Example 4 |
|---|---|---|---|---|
| Process Feed (lb/hr) | 1,000 | 1,000 | 1,000 | 1,000 |
| HFC-32 (wt %) | 99.99 | 99.99 | 99.96 | 99.0 |
| ppm |  |  |  |  |
| HFC-143a | 100 | 100 | 100 | 0 |
| CFC-12 | 0 | 0 | 100 | 5,000 |
| CFC-115 | 0 | 0 | 100 | 5,000 |
| HFC-125 | 0 | 0 | 100 | 0 |
| Total # Column Stages | 100 | 100 | 100 | 100 |
| Process Stream Feed Stage # | 50 | 50 | 50 | 50 |
| Process Feed Temperature (° C.) | −10 | −10 | −15 | −15 |
| Operating Pressure (psia) | 84.7 | 84.7 | 84.7 | 84.7 |
| Distillate Temperature (° C.) | −9.9 | −9.9 | −10.1 | −13.1 |
| Bottoms Temperature (° C.) | −8.9 | −8.9 | −8.9 | −8.9 |
| Q Condenser (pcu/hr) | −818,700 | −221,500 | −810,200 | −622,300 |
| Q Reboiler (pcu/hr) | 819,100 | 221,700 | 812,600 | 624,700 |
| Reflux Flow (lb/hr) | 10,000 | 2,000 | 10,000 | 10,000 |
| HFC-32 Purity (wt %) | 99.9973 | 99.9973 | 99.992 | 99.9995 |
| ppm |  |  |  |  |
| CFC-12 | — | — | 0 | 5 |
| HFC-143a | 27 | 27 | 34 | — |
| CFC-115 | — | — | 0 | 0 |
| HFC-125 | — | — | 46 | — |
| % of HFC-32 Feed Recovered | 96.8 | 28.8 | 98.3 | 98.5 |

TABLE 10

Removal of Halocarbon from HFC-32 using n-Hexane as Extractive Agent

|  | Example 3 | Example 4 | Example 5 | Example 6 | Example 7 | Example 8 |
|---|---|---|---|---|---|---|
| Process Feed (lb/hr) | 1,000 | 1,000 | 1,000 | 1,000 | 1,000 | 1,000 |
| HFC-32 (wt %) | 99.99 | 99.99 | 99.98 | 99.96 | 99.96 | 99.0 |
| ppm |  |  |  |  |  |  |
| HFC-143a | 0 | 100 | 100 | 100 | 100 | 0 |
| CFC-12 | 100 | 0 | 100 | 100 | 100 | 5,000 |
| CFC-115 | 0 | 0 | 0 | 100 | 100 | 5,000 |
| HFC-125 | 0 | 0 | 0 | 100 | 100 | 0 |
| Total # Column Stages | 47 | 69 | 69 | 69 | 69 | 69 |
| Extractive Agent Feed Stage # | 13 | 13 | 13 | 13 | 13 | 13 |
| Process Stream Feed Stage # | 35 | 52 | 52 | 52 | 52 | 52 |
| Process Feed Temperature (° C.) | −15 | −15 | −15 | −15 | −15 | −15 |
| Extractant feed Temperature (° C.) | −15 | −15 | −15 | −15 | −15 | −15 |
| Operating Pressure (psia) | 84.7 | 84.7 | 84.7 | 84.7 | 84.7 | 84.7 |
| Distillate Temperature (° C.) | −9.9 | −9.9 | −9.9 | −9.9 | −9.9 | −9.9 |
| Bottoms Temperature (° C.) | 129.9 | 138.3 | 138.3 | 138.6 | 139.0 | 138.2 |
| Q Condenser (pcu/hr) | −136,200 | −138,700 | −138,700 | −138,700 | −138,700 | −162,400 |
| Q Reboiler (pcu/hr) | 202,500 | 770,900 | 770,900 | 1,043,000 | 1,950,100 | 950,200 |

TABLE 10-continued

Removal of Halocarbon from HFC-32 using n-Hexane as Extractive Agent

|  | Example 3 | Example 4 | Example 5 | Example 6 | Example 7 | Example 8 |
|---|---|---|---|---|---|---|
| Reflux Flow (lb/hr) | 670 | 700 | 700 | 700 | 700 | 1,000 |
| Extractive Agent Flow (lb/hr) | 760 | 7,000 | 7,000 | 10,000 | 20,000 | 8,730 |
| HFC-32 Purity (wt %) | 99.9994 | 99.9973 | 99.9973 | 99.9922 | 99.9964 | 99.9995 |
| ppm |  |  |  |  |  |  |
| CFC-12 | 5 | — | 0 | 0 | 0 | 0 |
| HFC-143a | — | 26 | 26 | 8 | 0 | — |
| CFC-115 | — | — | — | 0 | 0 | 5 |
| HFC-125 | — | — | — | 69 | 36 | — |
| n-Hexane | 1 | 1 | 1 | 1 | 1 | 0.1 |
| % of HFC-32 Feed Recovered | 99.8 | 99.8 | 99.8 | 99.8 | 99.8 | 99.8 |

TABLE 11

Removal of CFC-12 and HFC-143a from HFC-32 using n-Pentane as Extractive Agent

|  | Example 9 | Example 10 | Example 11 |
|---|---|---|---|
| Process Feed (lb/hr) | 1,000 | 1,000 | 1,000 |
| HFC-32 (wt %) | 99.99 | 99.99 | 99.98 |
| ppm |  |  |  |
| HFC-143a | 0 | 100 | 100 |
| CFC-12 | 100 | 0 | 100 |
| Total # Column Stages | 69 | 69 | 69 |
| Extractive Agent Feed Stage # | 36 | 36 | 36 |
| Process Stream Feed Stage # | 52 | 52 | 52 |
| Process Feed Temperature (° C.) | −15 | −15 | −15 |
| Extractant feed Temperature (° C.) | −15 | −15 | −15 |
| Operating Pressure (psia) | 84.7 | 84.7 | 84.7 |
| Distillate Temperature (° C.) | −9.9 | −9.9 | −9.9 |
| Bottoms Temperature (° C.) | 99.4 | 100.5 | 100.5 |
| Q Condenser (pcu/hr) | −440,900 | −440,900 | −440,900 |
| Q Reboiler (pcu/hr) | 526,300 | 795,800 | 795,800 |
| Reflux Flow (lb/hr) | 4,400 | 4,400 | 4,400 |
| Extractive Agent Flow (lb/hr) | 1,264 | 5,302 | 5,302 |
| HFC-32 Purity (wt %) | 99.9994 | 99.9974 | 99.9974 |
| ppm |  |  |  |
| CFC-12 | 5 | — | 0 |
| HFC-143a | — | 25 | 25 |
| n-Pentane | 1 | 1 | 1 |
| % of HFC-32 Feed Recovered | 99.8 | 99.8 | 99.8 |

TABLE 12

Removal of Halocarbon from HFC-32 using Methanol, Methylene Chloride, and Acetone as Extractive Agents

| Extractive Agent | Example 12 Methanol | Example 13 Methanol | Example 14 Methylene Chloride | Example 15 Acetone | Example 16 Acetone |
|---|---|---|---|---|---|
| Process Feed (lb/hr) | 1,000 | 1,000 | 1,000 | 1,000 | 1,000 |
| HFC-32 (wt %) | 99.96 | 99.96 | 99.96 | 99.96 | 99.96 |
| ppm |  |  |  |  |  |
| HFC-143a | 100 | 100 | 100 | 100 | 100 |
| CFC-12 | 100 | 100 | 100 | 100 | 100 |
| CFC-115 | 100 | 100 | 100 | 100 | 100 |
| HFC-125 | 100 | 100 | 100 | 100 | 100 |
| Total # Column Stages | 69 | 69 | 69 | 69 | 69 |
| Extractive Agent Feed Stage # | 10 | 10 | 10 | 10 | 10 |

TABLE 12-continued

Removal of Halocarbon from HFC-32 using Methanol, Methylene Chloride, and Acetone as Extractive Agents

| Extractive Agent | Example 12 Methanol | Example 13 Methanol | Example 14 Methylene Chloride | Example 15 Acetone | Example 16 Acetone |
|---|---|---|---|---|---|
| Process Stream Feed Stage # | 52 | 52 | 52 | 52 | 52 |
| Process Feed Temperature (° C.) | −15 | −15 | −15 | −15 | −15 |
| Extractant feed Temperature (° C.) | −15 | −15 | −15 | −15 | −15 |
| Operating Pressure (psia) | 84.7 | 84.7 | 84.7 | 84.7 | 84.7 |
| Distillate Temperature (° C.) | −11.1 | −11.1 | −10.9 | −11.1 | −11.1 |
| Bottoms Temperature (° C.) | 61.8 | 90.8 | 36.1 | 90.0 | 104.3 |
| Q Condenser (pcu/hr) | −38,900 | −38,600 | −38,700 | −37,600 | −37,500 |
| Q Reboiler (pcu/hr) | 541,000 | 1,421,900 | 204,500 | 647,300 | 1,383,700 |
| Reflux Flow (lb/hr) | 500 | 500 | 500 | 500 | 500 |
| Extractive Agent Flow (lb/hr) | 10,000 | 20,000 | 10,000 | 10,000 | 20,000 |
| HFC-32 Purity (wt %) | 99.982 | 99.986 | 99.982 | 99.9965 | 99.9989 |
| ppm | | | | | |
| CFC-12 | 55 | 31 | 100 | 7 | 1 |
| HFC-143a | 22 | 5 | 79 | 25 | 9 |
| CFC-115 | 0 | 0 | 0 | 0 | 0 |
| HFC-125 | 100 | 100 | 2 | 3 | 1 |
| % of HFC-32 Feed Recovered | 99.8 | 99.8 | 99.8 | 99.8 | 99.8 |

What is claimed is:

1. A process for separating difluoromethane (HFC-32) from a first mixture consisting essentially of difluoromethane (HFC-32) and dichlorodifluoromethane (CFC-12), comprising the steps of:
   contacting the first mixture with a hydrocarbon extractive agent having from 5 to 9 carbon atoms and having a normal boiling point greater than about 30° C. and less than about 155° C. to form a second mixture;
   separating difluoromethane (HFC-32) from dichlorodifluoromethane (CFC-12) by distilling the second mixture in an extractive distillation zone; and
   recovering difluoromethane (HFC-32) substantially free of dichlorodifluoromethane (CFC-12) as an overhead product, and recovering said extractive agent and dichlorodifluoromethane (CFC-12) from the bottom of said extractive distillation zone.

2. The process of claim 1 wherein the hydrocarbon extractive agent is selected from the group consisting of n-pentane, 2-methylpentane, 3-methylpentane, cyclopentane, methylcyclopentane, n-hexane, cyclohexane and n-heptane.

3. The process of claim 1 wherein the difluoromethane (HFC-32) recovered from the second mixture contains less than about 50 ppmw dichlorodifluoromethane (CFC-12).

4. The process of claim 1 wherein the difluoromethane (HFC-32) recovered from the second mixture contains less than about 0.1 ppmw dichlorodifluoromethane (CFC-12).

5. A process for separating difluoromethane (HFC-32) from a first mixture consisting essentially of difluoromethane (HFC-32) and dichlorodifluoromethane (CFC-12), comprising the steps of:
   contacting the first mixture with an extractive agent selected from the group consisting of:
   oxygen-containing extractive agents consisting of alcohols having a normal boiling point greater than about 60° C. and less than about 100° C. and represented by the formula $C_xH_{2x+1}OH$, wherein x is from 1 to 3, and ketones having a normal boiling point greater than about 50° C. and less than about 110° C. and represented by the formula $C_yH_{2y+1}COC_zH_{2z+1}$, wherein y and z are 1 or greater and y+z is at most 5, and
   chlorocarbon extractive agents consisting of chlorocarbons having a normal boiling point greater than about 39° C. and less than about 150° C. and represented by the formula $C_sH_{2s+2-t}Cl_t$, wherein s is 1 or 2 and t is from 2 to 4 to form a second mixture;
   separating difluoromethane (HFC-32) from dichlorodifluoromethane (CFC-12) by distilling the second mixture in an extractive distillation zone; and
   recovering difluoromethane (HFC-32) substantially free of dichlorodifluoromethane (CFC-12), together with said extractive agent from the bottom of said extractive distillation zone.

6. The process of claim 5 wherein the oxygen-containing extractive agent is selected from the group consisting of methanol, ethanol, propanol, iso-propanol, propanone, and butanone.

7. The process of claim 5 wherein the chlorocarbon extractive agent is methylene chloride.

8. The process of claim 5 wherein the difluoromethane (HFC-32) recovered from the second mixture contains less than about 50 ppmw dichlorodifluoromethane (CFC-12).

9. The process of claim 5 wherein the difluoromethane (HFC-32) recovered from the second mixture contains less than about 0.1 ppmw dichlorodifluoromethane (CFC-12).

10. A process for separating difluoromethane (HFC-32) from a first mixture consisting essentially of difluoromethane (HFC-32) and 1,1,1-trifluoroethane (HFC-143a), comprising the steps of:

contacting the first mixture with a hydrocarbon extractive agent having from 5 to 9 carbon atoms and having a normal boiling point greater than about 30° C. and less than about 155° C. to form a second mixture;

separating difluoromethane (HFC-32) from 1,1,1-trifluoroethane (HFC-143a) by distilling the second mixture in an extractive distillation zone; and recovering difluoromethane (HFC-32) substantially free of 1,1,1-trifluoroethane (HFC-143a) as an overhead product, and recovering said extractive agent and 1,1,1-trifluoroethane (HFC-143a) from the bottom of said extractive distillation zone.

11. The process of claim 10 wherein the hydrocarbon extractive agent is selected from the group consisting of n-pentane, 2-methylpentane, 3-methylpentane, cyclopentane, methylcyclopentane, n-hexane, cyclohexane and n-heptane.

12. The process of claim 10 wherein the difluoromethane (HFC-32) recovered from the second mixture contains less than about 50 ppmw 1,1,1-trifluoroethane (HFC-143a).

13. The process of claim 10 wherein the difluoromethane (HFC-32) recovered from the second mixture contains less than about 0.1 ppmw 1,1,1-trifluoroethane (HFC-143a).

14. A process for separating difluoromethane (HFC-32) from a first mixture consisting essentially of difluoromethane (HFC-32) and 1,1,1-trifluoroethane (HFC-143a), comprising the steps of:

contacting the first mixture with an extractive agent selected from the group consisting of:

ketones having a normal boiling point greater than about 50° C. and less than about 110° C. and represented by the formula $C_yH_{2y+1}COC_zH_{2z+1}$, wherein y and z are 1 or greater and y+z is at most 5, and chlorocarbon extractive agents consisting of chlorocarbons having a normal boiling point greater than about 39° C. and less than about 150° C. and represented by the formula $C_5H_{2s+2-t}Cl_t$, wherein s is 1 or 2 and t is from 2 to 4 to form a second mixture;

separating difluoromethane (HFC-32) from 1,1,1-trifluoroethane (HFC-143a) by distilling the second mixture in an extractive distillation zone; and recovering difluoromethane (HFC-32) substantially free of 1,1,1-trifluoroethane (HFC-143a), together with said extractive agent from the bottom of said extractive distillation zone.

15. The process of claim 14 wherein the ketone extractive agent is selected from the group consisting of propanone and butanone.

16. The process of claim 14 wherein the chlorocarbon extractive agent is methylene chloride.

17. The process of claim 14 wherein the difluoromethane (HFC-32) recovered from the second mixture contains less than about 50 ppmw 1,1,1-trifluoroethane (HFC-143a).

18. The process of claim 14 wherein the difluoromethane (HFC-32) recovered from the second mixture contains less than about 0.1 ppmw 1,1,1-trifluoroethane (HFC-143a).

19. A process for separating difluoromethane (HFC-32) from a first mixture consisting essentially of difluoromethane (HFC-32) and chloropentafluoroethane (CFC-115), comprising the steps of:

contacting the first mixture with a hydrocarbon extractive agent having from 5 to 9 carbon atoms and having a normal boiling point greater than about 30° C. and less than about 155° C. to form a second mixture;

separating difluoromethane (HFC-32) from chloropentafluoroethane (CFC-115) by distilling the second mixture in an extractive distillation zone; and recovering difluoromethane (HFC-32) substantially free of chloropentafluoroethane (CFC-115) as an overhead product, and recovering said extractive agent and chloropentafluoroethane (CFC-115) from the bottom of said extractive distillation zone.

20. The process of claim 19 wherein the hydrocarbon extractive agent is selected from the group consisting of n-pentane, 2-methylpentane, 3-methylpentane, cyclopentane, methylcyclopentane, n-hexane, cyclohexane and n-heptane.

21. The process of claim 19 wherein the difluoromethane (HFC-32) recovered from the second mixture contains less than about 50 ppmw chloropentafluoroethane (CFC-115).

22. The process of claim 19 wherein the difluoromethane (HFC-32) recovered from the second mixture contains less than about 0.1 ppmw chloropentafluoroethane (CFC-115).

23. A process for separating difluoromethane (HFC-32) from a first mixture consisting essentially of difluoromethane (HFC-32) and chloropentafluoroethane (CFC-115), comprising the steps of:

contacting the first mixture with an extractive agent selected from the group consisting of:

oxygen-containing extractive agents consisting of alcohols having a normal boiling point greater than about 60° C. and less than about 100° C. and represented by the formula $C_xH_{2x+1}OH$, wherein x is from 1 to 3, and ketones having a normal boiling point greater than about 50° C. and less than about 110° C. and represented by the formula $C_yH_{2y+1}COC_zH_{2z+1}$, wherein y and z are 1 or greater and y+z is at most 5, and chlorocarbon extractive agents consisting of chlorocarbons having a normal boiling point greater than about 39° C. and less than about 150° C. and represented by the formula $C_5H_{2s+2-t}Cl_t$, wherein s is 1 or 12 and t is from 2 to 4 to form a second mixture;

separating difluoromethane (HFC-32) from chloropentafluoroethane (CFC-115) by distilling the second mixture in an extractive distillation zone; and recovering difluoromethane (HFC-32) substantially free of chloropentafluoroethane (CFC-115), together with said extractive agent from the bottom of said extractive distillation zone.

24. The process of claim 23 wherein the oxygen-containing extractive agent is selected from the group consisting of methanol, ethanol, propanol, iso-propanol, propanone, and butanone.

25. The process of claim 23 wherein the chlorocarbon extractive agent is methylene chloride.

26. The process of claim 23 wherein the difluoromethane (HFC-32) recovered from the second mixture contains less than about 50 ppmw chloropentafluoroethane (CFC-115).

27. The process of claim 23 wherein the difluoromethane (HFC-32) recovered from the second mixture contains less than about 0.1 ppmw chloropentafluoroethane (CFC-115).

* * * * *